United States Patent [19]

Clipper et al.

[11] Patent Number: 4,684,517

[45] Date of Patent: Aug. 4, 1987

[54] MOUTHRINSE COMPOSITION CONTAINING HYDROGEN PEROXIDE AND FLUORIDE

[75] Inventors: Donald Clipper, Belle Mead; James Norfleet, Plainfield, both of N.J.

[73] Assignee: Colgate-Palmolive Company, New York, N.Y.

[21] Appl. No.: 913,584

[22] Filed: Sep. 30, 1986

Related U.S. Application Data

[63] Continuation of Ser. No. 697,614, Feb. 4, 1985, abandoned, which is a continuation-in-part of Ser. No. 579,835, Feb. 13, 1984, Pat. No. 4,537,778, which is a continuation-in-part of Ser. No. 455,388, Jan. 3, 1983, Pat. No. 4,431,631.

[51] Int. Cl.$^4$ ............... A61K 7/18; A61K 7/20; A61K 33/16
[52] U.S. Cl. ........................ 424/52; 424/53; 424/151
[58] Field of Search ............ 424/52, 53, 151

[56] References Cited

U.S. PATENT DOCUMENTS

| | | | |
|---|---|---|---|
| 2,054,742 | 9/1936 | Elbel | 424/53 |
| 4,206,198 | 6/1980 | Schmolka | 424/49 |
| 4,226,851 | 10/1980 | Sompayrac | 424/53 |
| 4,289,754 | 9/1981 | Dhabhar et al. | 424/52 |
| 4,289,755 | 9/1981 | Dhabhar | 424/52 |
| 4,343,785 | 8/1982 | Schmolka | 424/52 |
| 4,348,381 | 9/1982 | Gaffar et al. | 424/52 |
| 4,396,599 | 8/1983 | Sipos | 424/52 |
| 4,430,323 | 2/1984 | Silver | 424/52 |
| 4,469,674 | 9/1984 | Shah et al. | 424/52 |
| 4,476,107 | 10/1984 | Schmolka | 424/52 |

*Primary Examiner*—Shep K. Rose
*Attorney, Agent, or Firm*—Herbert S. Sylvester; Murray M. Grill; Norman Blumenkopf

[57] ABSTRACT

An aqueous storage-stable mouthwash composition, optionally in the form of a gel and optionally containing special wintergreen or cinnamon flavor mixtures, comprising about 0.5 to about 5% by weight of hydrogen peroxide and about 0.01 to about 2% by weight of a compound providing fluoride or fluoride-containing ions in the composition.

19 Claims, No Drawings

MOUTHRINSE COMPOSITION CONTAINING HYDROGEN PEROXIDE AND FLUORIDE

This application is a continuation of application Ser. No. 697,614 filed Feb. 4, 1985 and now abandoned, which was a continuation-in-part of application Ser. No. 597,835 filed Feb. 13, 1984 and now U.S. Pat. No. 4,537,778, which was in turn a continuation-in-part of application Ser. No. 455,388 filed Jan. 3, 1983 and now U.S. Pat. No. 4,431,631.

This invention relates to an oral preparation and especially to an aqueous peroxide mouthwash or mouthrinse solution, gel or paste, containing a fluoride.

It has long been recognized in the art that hydrogen peroxide and other peroxygen-containing agents are effective in curative and/or prophylatic treatments with respect to caries, dental plaque, gingivitis, periodontitis, mouth odor, tooth stains, recurrent aphthous ulcers, denture irritations, orthodontic appliance lesions, post-extraction and postperiodantal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. The swishing action of a mouthrinse enhances this inherent chemomechanical action. Such action has been recommended for delivery of other agents into infected gingival crevices. Peroxide mouthrinses and other oral preparations prevent colonization and multiplication of anaerobic bacteria known to be associated with periodontal disease. Peroxygen-containing gels or pastes are indicated and/or desirable where it is required to selectively treat areas for more than a few seconds, such gels and pastes tending to remain at the site of application for a time sufficient for the peroxide to manifest its maximum effectiveness.

It is however also known that most peroxy compounds such as hydrogen peroxide and metal peroxides such as magnesium peroxide in such oral compositions, by interaction with other common excipients therein, tend to be unstable in storage, continuously losing the capacity to release active or nascent oxygen over relatively short periods of time, and tend to diminish or destroy the desired function of such excipients. Among such excipients are flavors and coloring agents added to enhance the acceptability of the preparations to those in need of an oral peroxidizing treatment. Numerous proposals have been made for solving the aforementioned problems, including encapsulating the peroxide compound and/or the peroxide-sensitive excipients, using more stable but more expensive peroxy compounds such as organic peroxides and peroxydiphosphate salts (e.g. the tetrapotassium salt), etc. In addition such flavored and/or colored peroxide products exhibit a gradual decrease in pH of from about 1 to 3 pH units.

It is an object of this invention to provide oral preparation which will not be subject to one or more of the aforementioned disadavantages and deficiencies. Another object of this invention is the provision of a foaming oxygenating oral preparation in ready-to-use form having a pleasant flavor and/or color and enhanced stability in storage. Still another object of this invention is the provision of a mouthrinse having a basis of the readily available, highly effective and economical hydrogen peroxide. Still a further object of this invention is provision of an oxygenating oral preparation containing an anti-caries agent such as fluoride. Yet a further object of this invention is the provision of an oral oxygenating preparation in the form of a gel, also with an anti-caries agent e.g. fluoride. Other objects and advantages will appear as the description proceeds.

The attainment of one or more of the above objects is made possible by this invention which comprises:
an aqueous oral preparation containing, approximately by weight: from about 0.5 to about 5% by weight of hydrogen peroxide and from about 0.01 to about 2% by weight of a compound providing fluoride or fluoride-containing ions in the aqueous composition, and preferably also containing an effective flavoring amount of a flavor selected from the group consisting of
(1) wintergreen flavor containing methyl salicylate and menthol in a weight ratio of about 3:1 to 5:1, and
(2) a cinnamon flavor composition comprising about 6–9% menthol, 32–38% cinnamic aldehyde and 6–9% clove oil.

The aforementioned component "B" flavors have surprisingly been found to be satisfactorily stable and compatible in the presence of hydrogen peroxide, in contrast to other flavors, e.g. fruity flavors such as orange, lemon and lime, and even minty flavors other than the aforesaid b1 component wintergreen flavor, such as peppermint and spearmint. Effective flavor amounts are as desired, typically ranging from about 0.05 to 1.0%, preferably about 0.1 to 0.5%, by weight of the oral composition.

It is generally desirable, and often preferred to include numerous adjuvants to the basic compositions of this invention. These include (C) ethanol; (D) polyhydric alcohols such as glycerol and sorbitol; (E) surfactants, especially nonionics, and of these, those which have been found to have acceptable stability in the aqueous peroxygen environment; (F) a sweetener; (G) anti-caries agents; (H) thickeners; (I) preservatives; (J) coloring agents; and the like.

With reference to the ethyl alcohol a convenient amount is 1 to 5% by weight based on the weight of the total composition, with 3–10% being a preferred range. The polyhydric alcohol (D) may range from about 1 to 20% by weight, with 3–15% being preferred.

Sorbitol is preferred as the component D polyhydric alcohol since although glycerin is sufficiently compatible with the other components, particularly the hydrogen peroxide, it interferes with at least one common method for analysis of the peroxide content. Component D serves hymectant, carrier (with the ethanol) and viscosity-control agent.

The component E surfactant, which is preferably nonionic comprises, in the more preferred embodiments, two general types of surfactants; those known under the Tween and other trademarks and those block polymers available under the Pluronic trademarks. The former (Tween) surfactants are mixtures of $C_{10-18}$ fatty acid esters of sorbitol (and sorbitol anhydrides), consisting predominantly of the monester, condensed with about 10–30, preferably about 20, moles of ethyleneoxide. The fatty acid (aliphatic hydrocarbyl monocarboxylic acid) may be saturated or unsaturated, e.g. lauric, palmitic, stearic, oleic acids. Polysorbate 20 (e.g. Tween 20) is especially preferred, commonly referred to as polyoxyethylene (20) sorbitan monolaurate. The Pluronic surfactants are straight chain polymers containing a hydrophobic (water insoluble) polyoxypropylene moiety polyoxyethylenated at both ends with sufficient water-solubilizing oxyethylene groups to achieve the desired water-solubility, HLB, (hydrophyliclipophylic balance) and dispersing surfactant activity. The solid F series of Pluronics are preferred in which the molecular weight of the polyoxypropylene moiety ranges from about 950 to 4,000 and constitutes about 20–30% of the molecule (i.e. 80–70% polyoxyethylene in the molecule). Pluronic F 108 is especially preferred, in which the said hydrophobic moiety has a molecular weight of about 3250 and constitutes about 2% of the molecule. This surfactant has a molecular weight of about 14,000–16,000.

The surfactant components serve as solubilizing, dispersing, emulsifying, wetting and viscosity-control agents and when used in certain combinations, are especially effective to solubilize the flavor.

A particularly useful combination of surfactants is one where at least one surfactant is of the Pluronic type and at least one is of the polysorbate type.

For the aforementioned functions of solubilizing, dispersing, emulsifying, wetting and viscosity-control, it is preferred to use from about 0.1% to about 10% by weight of surfactant; more preferred range is about 0.2% to about 6% and a most preferred range is from about 0.5 to about 5%.

Where combination of Pluronic and Polysorbate surfactants are used they may be employed in weight ratios of from about 20:1 to about 1:10 and preferably from about 10:1 to about 1:5.

As described above the compositions of this invention may contain other functional agents such as anticaries agents and the like. Fluorine-providing anticaries compounds optionally present in these solutions may be partially or fully water-soluble. They are characterized by their ability to release fluorine-containing ions in water and by substantial freedom from reaction with other compounds of the oral preparation. Among these materials are inorganic fluoride salts such as ammonium fluoride, calcium fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of the fluorine-providing compound is dependent to some extent upon the type of compound, its solubility, and the type of oral preparation, but it must be a nontoxic amount. An amount of such compound which releases a maximum of about 1% of fluoride ion by weight of the preparation is considered satisfactory. Any suitable minimum amount of such compound may be used, but it is preferable to employ sufficient compound to release about 0.005 to 1%, and preferably about 0.1% of fluoride ion. Typically, especially in the cases of MFP, alkali metal fluorides and stannous fluoride, this component is optionally present in these compositions in an amount of about 0.01 to 2 wt. %, preferably about 0.05 to 1 wt. %, especially about 0.76 wt. %.

It has been found that in peroxygen compound-containing compositions, and particularly in aqueous hydrogen peroxide, the pH equilibriates generally 1 to 3 pH units below the initial pH of the composition as it is prepared. This equilibrium value may occur from several months to a matter of a year or more later and it occurs in a sealed environment (i.e. not exposed to the atmosphere), as further described below. In the fluoride-containing composition of this invention it has been found that the equilibrium pH is much closer to the initially prepared pH with the maximum decrease being less than 0.5 pH units and the equilibrium value somewhat less than that. It is quite surprising that the presence of a fluoride, such as sodium fluoride, which is a neutral salt should have this pH stabilizing effect on aqueous peroxygen systems.

A coloring agent is also often desirable for enhanced appearance and acceptability, but should be carefully selected for compatibility with the other named components, particularly the hydrogen peroxide. Green coloring agents for example have been generally found to be unacceptable in this regard. FD & C Blue No. 1 and Red No. 40 have been found to satisfy the requirements of this invention, employed in effective coloring amounts as desired, typically in concentrations of about 0.0002 to 0.004% by weight in the solution.

A preferred component F sweetener compound is saccharin, especially sodium saccharin, but other known orally acceptable sweetener compounds may be employed, typically in concentrations of about 0.01 to 5 wt.%, such as xylitol, sodium cyclamate, perillartine, D-tryptophan, aspartame, dihydrochalcones and the like.

One preferred form of the oral compositions of this invention is as a solution in an aqueous and preferably an aqueousethyl alcohol carrier. A typical mode of preparation involves judiciously mixing the selected components for proper solubilization in the carrier medium (e.g. ethanol/polyhydric alcohol/water), any coloring agent and hydrogen peroxide in order being preferably added after any of the other selected components.

As pointed out above one may incorporate into the oral compositions of this invention any of the conventional preservatives (e.g. in weight amounts up to about 5% and preferably about 0.01% to about 1%) which are pharmaceutically acceptable.

Further one may formulate the compositions as gels or pastes utilizing, preferably peroxide-stable thickening and gelling agents. Useable agents include xanthan gum, guar gum, locust gum, carboxylic interpolymers as disclosed in U.S. Pat. No. 2,798,053, a water soluble carboxymethyl cellulose such as sodium carboxymethyl cellulose, and Pluronic Polyols particularly of the "10" and "12" Series and of these especially the solid products with a hydrophobe of M.W. of about 3500 to 4000 and with from 30 to 80% hydrophilic polyoxyethylene groups. Examples of such Pluronic compounds are P103, P104, P105, P123 F108 and F127. The most preferred gelling agent is Pluronic F127. The amount of thickener or gelling agent may vary widely. As little as 1 or 2 or 3 or 4 or 5% may suffice for some applications whereas for most gels a most representative range would be 5 to 50% with 10 to 30 preferred and 15 to 25 most preferred.

The pH of the solutions and other pastes and gels of this invention generally ranges from about 4 to 7, and preferably about 5. Generally, the pH may be from 6 to 7 when the composition is first prepared and then slowly drop to an equilibrium pH of from about 4 to about 6.

The following examples of preferred embodiments of this invention are only illustrative. All amounts and proportions referred to herein and in the appended claims are by weight unless otherwise indicated. Typically, in preparing these exemplified formulations, the flavor is first added to the carrier liquid, e.g. ethanol, with agitation. The component E surfactants where used, are then slowly sprinkled in with constant stirring for about ten minutes or until all the surfactants are dissolved and the solution is clear. The component D polyhydric alcohol, if used, is then added slowly with stirring followed by addition of the optional component F sweetener, preferably previously solubilized in a little water. Coloring agent, hydrogen peroxide (in the form of a 35% aqueous solution), and the remainder of the water are then added in succession.

The pastes and gels may be prepared from the formulation liquids merely by adding the thickener and/or gelling agent and if necessary the peroxygen source to bring it up to specifications in the final formula. Alternatively, all of the ingredients are added as above for solution preparation except before adding the peroxide, the gelling agent and/or thickener in aliquot portion of water is added followed by the peroxide. In this procedure one may also add the flavors after the thickener rather than at the onset.

TABLE 1

|  | Examples (% w/v) | | | | | |
| --- | --- | --- | --- | --- | --- | --- |
|  | 1 | 2 | 3 | 4 | 5 | 6 |
| Ethanol[1] | 4.75 | 4.75 | 4.75 | 4.75 | 4.75 | 4.75 |
| Wintergreen Flavor[2] | 0.22 | 0.22 | 0.22 |  |  | 0.22 |
| Cinnamon Flavor[3] |  |  |  | 0.15 | 0.15 |  |
| Pluronic F108 | 1.0 | 1.0 | 1.0 | 1.0 | 1.0 | 1.0 |
| Polysorbate 20[4] | 0.6 | 0.6 | 0.6 | 0.6 | 0.6 | 0.6 |
| Sorbitol[5] | 10.5 |  | 10.5 | 10.5 |  |  |
| Glycerin |  | 5.0 |  |  | 5.0 | 5.0 |
| Sodium saccharin | 0.04 | 0.04 | 0.04 | 0.04 | 0.04 | 0.04 |
| FD & C Blue No. 1[6] | .0004 | .0004 |  |  |  |  |
| FD & C Red No. 40[6] |  |  |  | .002 | .002 |  |
| Hydrogen peroxide[7] | 1.5 | 1.5 | 1.5 | 1.5 | 1.5 | 1.5 |
| Purified Water (USP Deionized) | ← q.s. to 100 v. → | | | | | |

[1]in form of 95% soln
[2]80% methyl salicylate, 20% menthol
[3]7.5% menthol, 35% cinnamic aldehyde, 7.5% clove oil in propylene glycol soln
[4]Tween 20-polyoxyethylene (20) sorbitan monolaurate
[5]in form of 70% soln
[6]in form of 1% soln
[7]in form of 35% soln All the above-exemplified formulations represent satisfactory, pleasing, acceptable and effective foaming oxygenating mouthrinses having satisfactory storage stability with respect to flavor, color, appearance, taste, peroxy content and the like.

The foregoing examples are repeated except 18% of Pluronic F127 gelling agent is provided in formulations and in each instance good, "ringing" gel is produced. The gelling agent is mixed with a major amount (90%) of the formula water and polyhydride alcohol to which is added the alcohol, flavor and surfactant (F108 and polysorbate) mixture and finally the saccharin, colorant (s) and hydrogen peroxide. The temperature is generally maintained at around 0° C. (e.g. −5° to 10° C.) during preparation of water gelling agent mixture and also during addition of other ingredient to this mixture. These examples are 1a to 6a.

EXAMPLE 7

75 grams of a 70% aqueous solution of sorbitol, 2.0 mg. of Blue Dye #1 and 470 ml of water are mixed and cooled to 5° C. To the mixture first there is added 125 grams of Pluronic F127 and after dissolution thereof there are added 1.1 grams of Wintergreen Flavor (as in Examples 1–6) and 21.4 grams of 35% aqueous hydrogen peroxide (USP). The mixture is allowed to come to room temperature. The next day it is noted that a good gel has formed. The amount of gelling agent (i.e. Pluronic F127) is about 18% by weight.

EXAMPLE 8

Example 7 is repeated except that along with initial mixture of sorbitol, dye and water there is added 5 grams of Carbopol 934 (a carboxylated vinyl polymer). The resultant product after a few days is a "heavy syrup".

EXAMPLE 9

25 grams of 95% USP ethanol and 0.85 grams of Wintergreen flavor (0.68 g. methyl salicylate and 0.17 g. USP menthol) are mixed. To this is added 3.85 g. of Pluronic F108 and mixing is done for 20 minutes. Then 1.25 g. of water are added with mixing. 2.3 g. of Polysorbate 20 N.F. (non-ionic) is added and mixed for 10 minutes. To 2.85 g. of water are added 60 g. of 70% aqueous sorbitol (USP) and the temperature lowered to 0°–5° C. To this cold solution are added 100 g. of Pluronic F127. It is noted that temperature drops to −2° C. Mixing is done for 40 minutes. To this cold mixture is added the alcohol, flavor, Pluronic F108, and Polysorbate mixture. Then 0.15 g. of sodium saccharin (USP), 0.0015 g. FD & C Blue #1, and 21.43 g. of 35% aqueous hydrogen peroxide are added and well mixed for about 10 minutes. Excellent gel is formed.

EXAMPLE 10

A fluoride-containing mouthrinse of the following composition is prepared following the typical procedure hereinbefore mentioned:

| Alcohol USP 95% | 200.0 gm |
| --- | --- |
| Flavor (as in Ex. 1) | 4.0 gm |
| Pluronic F-108 | 40.0 gm |
| Sorbitol USP (70% aqueous solution) | 600.0 gm |
| Sodium Saccharin USP | 1.6 gm |
| FD & C Blue No. 1 (1% solution) | 2.8 gm |
| Hydrogen peroxide (35%) | 171.43 gm |
| Polysorbate 20 (as in Ex. 1) | 24.0 gm |
| Sodium Fluoride USP | 1.94 gm |
| Purified Water USP as to | 4000 cc |

As prepared the pH of the formulations is 5.11. After almost 4 months the pH has dropped to only 4.91 and after 10 months it is 4.72. At equilibrium (several months later) the pH is 4.75. In a similar batch but without the sodium fluoride, the pH which initially is 5.10, drops to 3.69 after 10 months and several months thereafter it has dropped a bit further to 3.65.

Similar results occur in systems without the flavor & color in one case and without the surfactants and/or saccharin in another case. The presence or absence of the alcohol does not affect the results.

This invention has been disclosed with respect to preferred embodiments, and various modifications and variations thereof obvious to those skilled in the art are to be included within the spirit and purview of this application and the scope of the appended claims.

We claim:
1. An aqueous storage-stable mouthwash composition comprising: from about 0.5 to about 5% by weight of hydrogen peroxide, and from about 0.01 to about 2% by weight of a compound providing fluoride or fluoride-containing ions in the aqueous composition.

2. A mouthwash composition according to claim 1 further including from about 3 to 10% by weight of ethanol.

3. A mouthwash composition according to claim 1 further including from about 1 to 20% by weight of polyhydric alcohol.

4. A mouthwash composition according to claim 1 further including from about 0.1% to about 10% non-ionic surfactant.

5. A mouthwash composition according to claim 1 wherein the amount of hydrogen peroxide is from about 1% to about 3%, and further including about 0.5 to 5% non-ionic surfactant, about 3-10% ethanol and about 3-15% polyhydric alcohol selected from glycerol and sorbitol.

6. A mouthwash composition according to claim 5 wherein the nonionic surfactant comprises from about 0.5% to 3% of a water soluble polyoxyethylenated-polyoxypropylene polyol and from about 0.3% to 2% of a water soluble polyoxyethylenated monoester of sorbitol with a $C_{10}$ to $C_{18}$ fatty acid.

7. An aqueous oral gel comprising the mouthwash composition of claim 1.

8. An aqueous oral gel according to calim 7 including from about 1% to about 50% of a gelling agent.

9. An aqueous oral gel according to claim 8 wherein the amount of gelling agent is from about 5% to 30% by weight of the gel.

10. An aqueous oral gel according to claim 9 wherein the gelling agent is a water-soluble polyoxyethylenated polyoxypropylene polyol.

11. An aqueous oral gel according to claim 10 wherein the gelling agent contains a polyoxypropylene hydrophobe of about 3,500-4,000 M.W. and about 30 to 80% of hydrophilic polyoxyethylene groups.

12. A mouthwash composition according to claim 1 further including a flavoring agent selected from the group consisting of:
 (1) wintergreen flavor containing methyl salicylate and menthol in a weight ratio of about 3:1 to 5:1, and
 (2) cinnamon flavor containing 6-9% menthol, 32-38% cinnamic aldehyde and 6-9% clove oil.

13. A mouthwash composition according to claim 1 including a coloring agent.

14. A method comprising rinsing the oral cavity with the mouthwash composition of claim 1.

15. A method comprising rinsing the oral cavity with the mouthwash composition of claim 5.

16. A method comprising rinsing the oral cavity with the mouthwash composition of claim 6.

17. A method comprising selectively treating areas of the oral cavity with the aqueous oral gel of claim 7.

18. A method comprising selectively treating areas of the oral cavity with the aqueous oral gel of claim 8.

19. A method comprising selectively treating areas of the oral cavity with the aqueous oral gel of claim 10.

* * * * *